(12) United States Patent
Liu et al.

(10) Patent No.: US 9,011,908 B2
(45) Date of Patent: Apr. 21, 2015

(54) PROGESTERONE SOLUTIONS FOR INCREASED BIOAVAILABILITY

(75) Inventors: Zhi Liu, Jamestown, NC (US); Saujanya L. Gosangari, Greensboro, NC (US); Dana S. Toops, Parkland, FL (US); Aqeel Fatmi, Greensboro, NC (US)

(73) Assignee: Banner Life Sciences LLC, High Point, NC (US)

( * ) Notice: Subject to any disclaimer, the term of this patent is extended or adjusted under 35 U.S.C. 154(b) by 867 days.

(21) Appl. No.: 12/752,629

(22) Filed: Apr. 1, 2010

(65) Prior Publication Data

US 2010/0255085 A1 Oct. 7, 2010

Related U.S. Application Data

(60) Provisional application No. 61/166,866, filed on Apr. 6, 2009.

(51) Int. Cl.
| | | |
|---|---|---|
| *A61P 5/34* | (2006.01) | |
| *A61K 9/48* | (2006.01) | |
| *A61K 31/57* | (2006.01) | |
| *A61K 47/12* | (2006.01) | |
| *A61K 47/14* | (2006.01) | |

(52) U.S. Cl.
CPC .............. *A61K 9/4858* (2013.01); *A61K 31/57* (2013.01); *A61K 47/12* (2013.01); *A61K 47/14* (2013.01)

(58) Field of Classification Search
None
See application file for complete search history.

(56) References Cited

U.S. PATENT DOCUMENTS

| | | | |
|---|---|---|---|
| 4,701,327 A * | 10/1987 | Henmi et al. ................. 424/455 | |
| 4,963,540 A | 10/1990 | Maxson et al. | |
| 5,645,856 A | 7/1997 | Lacy et al. | |
| 5,874,106 A * | 2/1999 | Adesunloye et al. ......... 424/456 |
| 6,096,338 A * | 8/2000 | Lacy et al. ..................... 424/455 |
| 6,638,522 B1 * | 10/2003 | Mulye ........................... 424/439 |
| 2006/0257472 A1* | 11/2006 | Nielsen ......................... 424/464 |
| 2007/0053869 A1* | 3/2007 | Sugiyama et al. .......... 424/78.38 |

FOREIGN PATENT DOCUMENTS

| | | |
|---|---|---|
| EP | 0 750 495 | 1/1997 |
| WO | 9524893 | 9/1995 |
| WO | 9709978 | 3/1997 |
| WO | WO 97/40823 | 11/1997 |
| WO | WO 99/08666 | 2/1999 |
| WO | WO 2004/030658 | 4/2004 |
| WO | WO 2005/072686 | 8/2005 |
| WO | WO 2006/102157 | 9/2006 |

OTHER PUBLICATIONS

International Search Report PCT/US2010/029625, mailed Mar. 3, 2011.

* cited by examiner

*Primary Examiner* — David J Blanchard
*Assistant Examiner* — Sarah Chickos
(74) *Attorney, Agent, or Firm* — Pabst Patent Group LLP

(57) ABSTRACT

Fill materials for hydrophobic drugs, such as progesterone, and methods of making and using thereof are described herein. The fill material contains the hydrophobic drug dissolved in one or more fatty acids. The concentration of the hydrophobic drug is typically from about 7% to about 50% by weight of the fill material. The concentration of the one or more fatty acids is from about 60% to about 95% by weight of the carrier. The formulation also contains an organic acid and one or both of one or more pharmaceutically acceptable alcohols and one or more pharmaceutically acceptable mono-, di-, or triesters of medium or long chain fatty acids. The fill material can be encapsulated in a hard or soft capsule. The formulations described herein have a higher dissolution rate and faster onset of dissolution compared to micronized progesterone suspended in an oil and thus should have increased bioavailability in vivo.

29 Claims, 2 Drawing Sheets

PROGESTERONE SOLUTIONS FOR INCREASED BIOAVAILABILITY

CROSS-REFERENCE TO RELATED APPLICATIONS

This application claims priority to U.S. Ser. No. 61/166,866 by Liu et al. entitled "*Progesterone Solutions for Increased Bioavailability*", filed on Apr. 6, 2009, which is incorporated by reference in its entirety, where permissible.

FIELD OF THE INVENTION

This invention is in the field of capsule fill materials containing hydrophobic drugs, particularly hydrophobic sex hormones, such as progesterone, which exhibit increased bioavailability when administered orally.

BACKGROUND OF THE INVENTION

Sex hormones are a class of compounds produced by the testicles, ovaries, brain, placenta, and/or adrenal glands, which play a major role in reproduction and sexual identity. One class of sex hormones is the steroidal hormones. Steroidal hormones are typically hydrophobic, having low solubility in aqueous solution, and low bioavailability in vivo.

Progesterone is a C-21 steroidal sex hormone involved in the female menstrual cycle, pregnancy (supports gestation) and embryogenesis of humans and other species. Progesterone belongs to a class of hormones called progestogens, and is the major naturally occurring human progestogen. Like other steroids, progesterone consists of four interconnected cyclic hydrocarbons. Progesterone is hydrophobic, having an aqueous solubility of 0.007±0.0 mg/ml. Progesterone is biosynthesized from pregnenolone, a derivative of cholesterol.

Progesterone and its analogues can be used to treat a variety of medical conditions, including acute diseases or disorders, as well as chronic diseases and disorders associated with long-term declines of natural progesterone levels. However, progesterone is poorly absorbed when administered orally. PROMETRIUM®, a commercially available progesterone formulation, is an attempt to overcome the poor oral bioavailability of progesterone (see the package insert for PROMETRIUM®). In PROMETRIUM®, the progesterone is micronized and suspended in an edible oil, such as peanut oil. However, clinical trials involving PROMETRIUM® showed significant interpatient and intrapatient variability. For example, a clinical trial involving postmenopausal women who were administered PROMETRIUM® once a day for five days resulted in the mean pharmacokinetic parameters listed in Table1 (see the package insert for PROMETRIUM®).

TABLE 1

Pharmacokinetic Parameters for PROMETRIUM ™
PROMETRIUM ™ Capsule Dose
(mean +/− standard deviation)

| Parameter | 100 mg | 200 mg | 300 mg |
|---|---|---|---|
| $C_{max}$ (ng/ml) | 17.3 ± 21.9$^a$ | 38.1 ± 37.8 | 60.6 ± 72.5 |
| $T_{max}$ (hrs) | 1.5 ± 0.8 | 2.3 ± 1.4 | 1.7 ± 0.6 |
| $AUC_{(0-10)}$ (ng * hr/mL) | 43.3 ± 30.8 | 101.2 ± 66.0 | 175.7 ± 170.3 |

The unusually high variability in the $C_{max}$ and $AUC_{(0-10)}$ (as evidenced by the large standard deviation) indicates that a significant percentage of patients are overdosed or receive a sub-optimal dose. PROMETRIUM™ is also known to exhibit significant intrapatient variability. Finally, the presence of peanut oil in the formulation excludes patients who are allergic to peanut oil.

Attempts to overcome the solubility problems associated with hydrophobic compounds, particularly steroids, have been described in the literature. For example, WO99/08666 by Glaxo Group, Ltd. describes solutions containing a therapeutically effective amount of an aza steroid and a fatty acid ester of glycerol or propylene glycol. The aza steroid is present in a concentration from 0.0025 to 2.5% by weight of the solution, more preferably from 0.025 to 1.5% by weight of the solution, with a dose of 0.1 to 10 mg. Aza steroids are synthetically derived steroids, not steroidal sex hormones. Further, the concentration of the steroid is very low, i.e., less than 2.5% by weight of the fill.

WO 2005/072686 by Stiefel Laboratories describes orally administrable softgels and fill compositions for use in treating various dermatological conditions. In one embodiment, the softgel capsule contains an internal, non-aqueous liquid phase containing a solution or suspension of a single, hydrophobic pharmacologically active agent effective to treat a dermatological disorder and one or more fatty acids or derivatives thereof, such as omega-3 fatty acids, DHA, docosapentaenoic acid, tetracosapentaenoic acid, tetracosahexaenoic acid, monounsaturated fatty acids, polyunsaturated fatty acids, saturated fatty acids, trans fatty acids, derivatives thereof, and mixtures thereof. Suitable classes of active agent include steroids. However, the '686 application does not disclose or suggest fill materials containing steroidal sex hormones, such as progesterone dissolved in a fatty acid solvent.

WO 2006/102157 by Ivax Pharmaceuticals S.R.O. describes soft gelatin capsules that encapsulate a water-insoluble active agent dissolved in a crystallization inhibitor. The inhibitor contains at least one monoacylglycerol compound whose acyl group is a fatty acid residue of 6-18 carbons. The concentration of the inhibitor is from 2 to 10% w/w of the fill (page 6, lines 9-12). The '157 application does not disclose or suggest a capsule containing a steroidal sex hormone dissolved in a fatty acid solvent, wherein the concentration of the fatty acid solvent is at least 50% by weight of the fill material.

U.S. Pat. No. 5,645,856 to Lacy, et al., describes a pharmaceutical composition containing progesterone in a carrier system containing a digestible oil and a pharmaceutically acceptable surfactant component for dispersing the oil in vivo. EP 0 750 495 to R.P. Scherer Technologies, Inc. describes a pharmaceutical composition containing a lipophilic surfactant component and a hydrophobic drug dispersed or dissolved in a digestible oil which contains a hydrophilic surfactant, where some or all of the oil is the lipophilic surfactant component. The '856 and '495 patents define "digestible oil" as an oil which is capable of undergoing de-esterification in the presence of pancreatic lipase in vivo under normal physiological conditions. The surfactant component may contain a fatty acid such as oleic acid. The '856 patent describes formulations containing up to 50% by weight of the drug. Although progesterone is included in the list of drugs which may be formulated, the concentration of progesterone in the examples does not exceed about 5% by weight.

WO 97/40823 by R.P. Scherer Ltd. describes the '856 patent to Lacy, et al., as achieving a maximum concentration of progesterone of about 4% which requires either a large dosage capsule or requires the dosage to be split into two capsules. In contrast, the '823 application seeks to address low solubilization of progesterone through pharmaceutical compositions containing a hydrophobic drug, a digestible oil, such as triglycerides or propylene glycol esters of medium chain length ($C_8$-$C_{12}$) and/or long ($C_{13}$-$C_{22}$) fatty acids, and propylene glycol monolaurate; a lipophilic surfactant containing a glyceride of $C_5$ to $C_{10}$ fatty acid; and a hydrophilic surfactant which is a polyoxyethylene hydrogenated castor oil. The '823 application discloses formulations that preferably do not contain unsaturated components. The '823 application describes progesterone formulations containing up to 6.5% by weight progesterone in solubilized form.

U.S. Pat. No. 4,963,540 to Maxson et al. describes pharmaceutical compositions suitable for oral administration containing micronized progesterone dispersed in an oil vehicle which is high in glycerides of polyunsaturated fatty acids. The fill materials can be used to fill capsules, such as softgel capsules. The capsules contain a dose of progesterone from 50-150 mg, particularly 90-110 mg. The oil vehicle is used in an amount ranging from 1.5-2.5 ml per one gram of progesterone. The fill material in the '540 patent is a dispersion, not a solution.

There exists a need for compositions containing higher concentrations of a sex hormone, such as progesterone, and which exhibit higher oral bioavailability, lower interpatient and intrapatient variability, and do not contain carriers which are unsuitable due to a high prevalence of adverse reactions when ingested.

Therefore, it is an object of the invention to provide compositions containing a sex hormone, such as progesterone, that exhibit: (1) increased oral bioavailability, compared to a formulation containing micronized drug suspended in a carrier; (2) lower interpatient and intrapatient variability compared to a formulation containing micronized drug suspended in a carrier, and (3) higher effective concentrations of the hormone; and methods of making and using thereof.

Additionally, it is an object of the invention to provide compositions which do not contain a carrier known to cause adverse reactions.

SUMMARY OF THE INVENTION

Fill materials containing hydrophobic active agents, such as the sex hormone progesterone, and methods of making and using thereof are described herein. The fill materials contain the hydrophobic active agent dissolved in a fatty acid-containing carrier composition. Suitable hydrophobic active agents include sex hormones, such as progesterone, in combination with one or more additional active agents. Exemplary fatty acids include, but are not limited to, oleic acid, linoleic acid, myristoleic acid, palmitoleic acid, arachidonic acid, and combinations thereof.

The concentration of the hydrophobic active agent is typically from about 6% to about 50% by weight of the fill material, preferably from 7% to about 40% of the fill material, preferably from about 7% to about 25% by weight of the fill material, more preferably from about 7% to about 20%, more preferably from about 7% to about 15% by weight of the fill material. In a preferred embodiment, the sex hormone is progesterone which is present from about 7% to about 15% by weight of the fill material, preferably from about 8% to about 12% by weight of the fill material, more preferably from about 9% to about 11% by weight of the fill material. The dose of progesterone is from about 100 mg to about 300 mg, more preferably from about 100 mg to about 200 mg. In one embodiment, the dose of progesterone is 100 mg, 200 mg, or 300 mg.

The concentration of the one or more fatty acids in the carrier composition is from about 60% to about 95% by weight of the fill material, preferably from 60% to about 90% by weigh of the fill materials, more preferably from about 60% to about 85% by weight of the fill material, most preferably from about 60% to about 80% by weight. In a preferred embodiment, the one or more fatty acids is oleic acid in a concentration from about 60% to about 95% by weight of the fill material, more preferably from about 65% to about 85% by weight of the fill material.

The carrier composition further contains one or more pharmaceutically acceptable organic acids selected from $C_1$ to $C_{12}$ acids. Suitable organic acids include, but are not limited to, lactic acid, acetic acid, glycolic acid, propionic acid, isobutyric acid, butyric acid, isovaleric acid, valeric acid, caproic acid, succinic acid and combinations thereof. The concentration of the one or more organic acids is from about 1 to about 20% by weight of the fill material, preferably from about 2 to about 18% by weight of the fill material, preferably from about 3% to about 15% by weight of the fill material, more preferably from about 5% to about 12% by weight of the fill material, most preferably from about 6% to about 12% by weight of the fill material.

The carrier composition also contains one or both of one or more pharmaceutically acceptable alcohols selected from $C_1$ to $C_6$ alcohols, and one or more pharmaceutically acceptable mono-, di-, or triesters of medium or long chain fatty acids. Suitable alcohols include, but are not limited to, ethanol, isopropanol, isobutanol, butanol, t-butanol, glycerol, propylene glycol and combinations thereof. The concentration of the alcohol is from about 1 to about 20% by weight of the fill material, preferably from about 2 to about 18% by weight of the fill material, preferably from about 5 to about 15% by weight of the fill material, more preferably from about 6% to about 15% by weight of the fill material, most preferably from about 8% to about 15% by weight of the fill material.

Suitable fatty acid esters include, but are not limited to, mono- and diglycerides of capric and caprylic acids; mono-, di-, and triglycerides of coconut oil; glyceryl monooleate, glyceryl monolinoleate; propylene glycol monocaprylate; propylene glycol caprylate; propylene glycol dicapryloca-prate; propylene glycol monolaurate; propylene glycol laurate; polyethoxylated fatty acid esters; polyethylene glycol monostearate; polyoxy stearate; polyethylene glycol hydroxystearate; macrogol hydroxystearate; and combinations thereof. The concentration of the ester is from about 1% to about 40% by weight of the fill material, preferably from about 5% to about 35% by weight of the fill material, preferably from about 10% to about 35% by weight of the fill material, more preferably from about 15% to about 35% by weight of the fill material, most preferably from about 20% to about 35% by weight of the fill material.

The fill material optionally further contains one or more additional excipients such as stabilizers, antioxidants, colorants, flavorings, which are typically present in fill formulations for capsules.

The fill material can be encapsulated in a hard or soft, gelatin or non-gelatin capsule. The capsule may be an enteric capsule, wherein the enteric polymer or polymers is a component of the capsule shell. Alternatively, the capsule can be coated with a modified release coating, such as a delayed release coating, a sustained release coating, or combinations thereof.

The compositions described herein provide improved dissolution in aqueous media in vitro compared to formulations of hydrophobic drugs suspended in an oil, such as peanut oil. In one embodiment, the compositions described herein release at least about 10%, 20%, 30%, 40%, 50%, 55%, 60%, 65%, 70%, 75%, 80%, 85%, 90%, or 95% of the drug in vitro after 5 minutes in 5% SDS in water or at least about 10%, 20%, 30%, 40%, 50%, 55%, 60%, 65%, 70%, 75%, 80%, 85%, 90%, or 95% of the drug in vitro after 15 minutes in 0.5% SDS in water. In another embodiment, the compositions described herein release at least about 15%, 20%, 25%, 30%, 35%, 40%, 45%, 50%, 55%, 60%, 65%, or 70% of the drug in vitro in fed state simulated intestinal fluid (FeSSIF) after 24 hours.

The capsules described herein can be administered to treat a variety of diseases or disorders. Progesterone can be used to support pregnancy in Assisted Reproductive Technology (ART) cycles such as In-vitro Fertilization (IVF). Progesterone can also be used to control anovulatory bleeding, to prepare uterine lining in infertility therapy, and to support early pregnancy. Patients with recurrent pregnancy loss due to inadequate progesterone production may receive progesterone. Progesterone is also used for the prevention of endometrial hyperplasia in nonhysterectomized postmenopausal women who are receiving conjugated estrogen tablets and for treatment of secondary amenorrhea.

The capsules described herein exhibit improved dissolution in aqueous media in vitro compared to formulations containing micronized progesterone suspended in an oil, such as peanut oil, such as commercially available formulations sold under the trademark PROMETRIUM®. For example, capsules (Formulation 5) containing progesterone dissolved in a fatty acid-based carrier containing CAPMUL® PG-8 (27.5% by weight of the composition), released over 90% of the progesterone after 5 minutes in 5% SDS in water compared to PROMETRIUMTNI PROMETRIUM®, which released negligible amounts of progesterone over the same time period. For capsules containing no CAPMUL® PG-8 (Formulation 1), over 80% of the progesterone was released after 15 minutes in 0.5% SDS in water compared to PROMETRIUM®, which released only negligible amounts of progesterone over the same time period. Moreover, the amount of progesterone released from a fatty-acid containing formulation in fed state simulated intestinal fluid (FeSSIF) was about 4 to 5 times higher than that released from PROMETRIUM® capsules. The cumulative release at the end of 24 hours from the fatty acid-containing formulation was about 51% versus less than about 10% from PROMETRIUM®.

The improved dissolution in vitro should result in improved bioavailability in vivo compared to micronized progesterone formulations.

DETAILED DESCRIPTION OF THE INVENTION

I. Definitions

Figure 1:
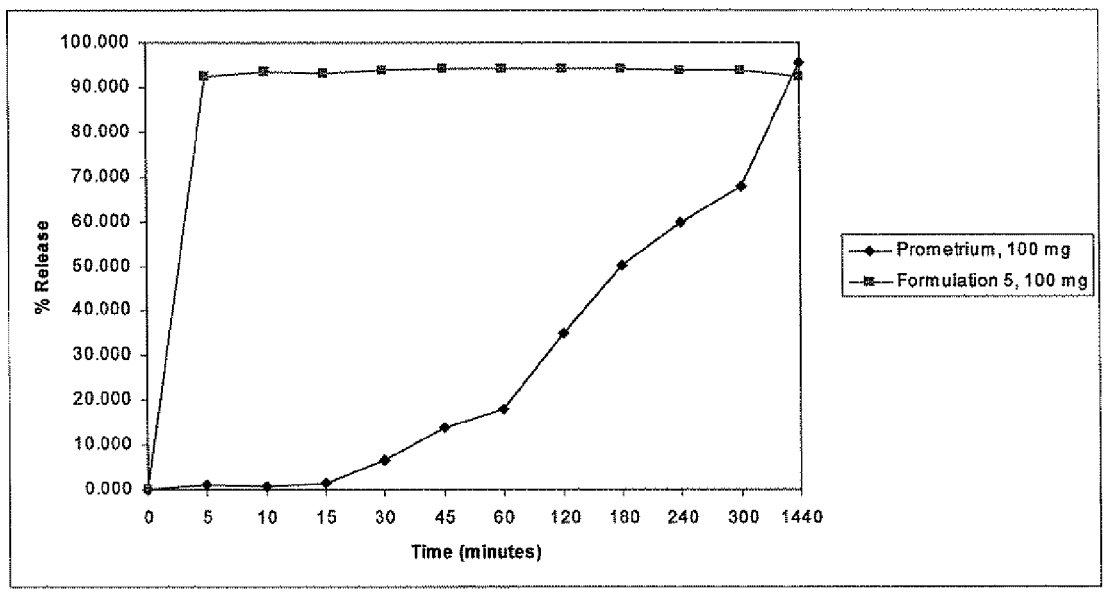
FIG. 1 is a graph comparing the in vitro release profile of progesterone (percent release) dissolved in an oleic acid-based vehicle and encapsulated in a two-piece hard shell capsule to the in vitro release profile of PROMETRIUM® (micronized progesterone suspended in peanut oil and encapsulated in a softgel capsule) in 5% sodium dodecyl sulfate (SDS) in water as a function of time (minutes) in a USP Apparatus II at 37±0.5° C. and 100 RPM.

"Sex hormone", as used herein, refers to chemicals produced by the testicles, ovaries, brain, placenta, and/or adrenal glands, which play a major role in reproduction and sexual identity. One class of sex hormones is the steroidal hormones. Examples of sex hormones include, but are not limited to, progesterone.

"Fatty acid", as used herein, refers to a molecules having the chemical formula R—C(=O)—OH. The fatty acid may contain one or more additional sites of unsaturation, such as carbon-carbon double bonds, carbon-carbon triple bonds, and combinations thereof.

"Medium chain fatty acid," as used herein, refers to a natural or synthetic fatty acid, or mixture thereof, typically having from about 6 to about 12 carbon atoms.

II. Compositions

A. Fill Materials

1. Sex Hormones

The fill materials described herein contain one or more sex hormones. Exemplary sex hormones include, but are not limited to, progesterone, alone or in combination with one or more other hormones. The concentration of the sex hormone is from about 6% to about 50% by weight of the fill material, preferably from 7% to about 40% of the fill material, preferably from about 7% to about 25% by weight of the fill material, more preferably from about 7% to about 20%, more preferably from about 7% to about 15% by weight of the fill material.

In a preferred embodiment, the sex hormone is progesterone. Progesterone is a C-21 steroid hormone involved in the female menstrual cycle, pregnancy (supports gestation) and embryogenesis of humans and other species. The concentration of progesterone is from about 7% to about 15% by weight of the fill material, preferably from about 8% to about 12% by weight of the fill material, more preferably from about 9% to about 11% by weight of the fill material. The dose of progesterone per capsule is preferably from about 100 mg to about 300 mg, more preferably from about 100 mg to about 200 mg. In one embodiment, the dose of progesterone is 100 mg, 200 mg, or 300 mg.

2. Carrier Composition (a) Fatty Acid Solvent(s)

The carrier composition in which the sex hormone is dissolved contains one or more pharmaceutically acceptable fatty acids. The one or more fatty acids have the general formula R—C(=O)—OH, wherein the R group contains from about 4 to about 20 carbons, preferably from about 8 to about 20 carbons, preferably from about 12 to about 20 carbons, more preferably from about 14 to about 20 carbons, most preferably from about 14 to about 18 carbons, and is fully saturated or contains one or more sites of unsaturation, in addition to the carbonyl group, such as carbon-carbon double bonds, carbon-carbon triple bonds, and combinations thereof. Exemplary fatty acids include, but are not limited to, oleic acid, linoleic acid, myristoleic acid, palmitoleic acid, arachidonic acid, and combinations thereof.

Hydrophobic sex hormones, such as progesterone, can be formulated into a stable solution at high concentration (i.e., about 10%, w/w) in a carrier system containing fatty acids, such as oleic acid. The concentration of the one or more fatty acids in the fill material is from about 60% to about 95% by weight of the fill material, preferably from about 60% to about 90% by weigh of the fill materials, more preferably from about 60% to about 85% by weight of the fill material, most preferably from about 60% to about 80% by weight. In a preferred embodiment, the one or more fatty acids is oleic acid in a concentration from about 60% to about 95% by weight of the fill material, more preferably from about 65% to about 80% by weight of the fill material, most preferably from about 65% to about 75% by weight of the fill material.

Alternatively, the amount of the fatty acids can be expressed as weight percent of the carrier composition (i.e., the fill material absent the active pharmaceutical ingredient). The concentration of the one or more fatty acids in the carrier composition is from about 60% to about 95% by weight of the carrier composition, preferably from about 65% to about 80% by weight of the carrier composition, more preferably from about 65% to 75% by weight of the carrier composition.

(b) Organic Acid

The carrier composition contains one or more pharmaceutically acceptable organic acids selected from $C_1$ to $C_{12}$ acids. Exemplary organic acids include, but are not limited to, lactic acid, acetic acid, glycolic acid, propionic acid, isobutyric acid, butyric acid, isovaleric acid, valeric acid, caproic acid, succinic acid, and combinations thereof. The organic acid may be present at a concentration from about 1% to about 20% by weight of the fill material, preferably from 2% to 18% by weight of the fill material, preferably from about 3% to about 15% by weight of the fill material, more preferably from about 5% to about 12% by weight of the fill material, most preferably from about 6% to about 12% by weight of the fill material.

Alternatively, the amount of organic acid(s) can be expressed as weight percent of the carrier composition (i.e., the fill material absent the active pharmaceutical ingredient). The concentration of the one or more organic acids in the carrier composition is from about 1% to about 20% by weight of the carrier composition, more preferably from 2% to 18% by weight of the carrier composition, and most preferably from about 3% to about 15% by weight of the carrier composition.

(c) Alcohol and/or Fatty Acid Ester

The carrier composition further contains one or more pharmaceutically acceptable alcohols and/or one or more pharmaceutically acceptable fatty acid esters. Suitable alcohols include, but are not limited to, $C_1$ to $C_6$ alcohols. Exemplary alcohols include, but are not limited to, pharmaceutically acceptable alcohols such as ethanol, isopropanol, isobutanol, butanol, t-butanol, glycerol, propylene glycol, and combinations thereof. When present, the concentration of the alcohol is from about 1% to about 20% by weight of the fill material, preferably from 2% to 18% by weight of the fill material, preferably from about 5 to about 15% by weight of the fill material, more preferably from about 6% to about 15% by weight of the fill material, most preferably from about 8% to about 15% by weight of the fill material.

Alternatively, the amount of alcohol(s) can be expressed as weight percent of the carrier composition (i.e., the fill material absent the active pharmaceutical ingredient). The concentration of the one or more alcohols in the carrier composition is from about 1% to about 20% by weight of the carrier composition, more preferably from 2% to 18% by weight of the carrier composition, and most preferably from about 5% to about 15% by weight of the carrier composition.

Suitable fatty acid esters include, but are not limited to, pharmaceutically acceptable mono-, di- or tri-esters of medium or long chain fatty acids. In one embodiment, the fatty acid ester is a synthetic fatty acid ester of medium or long chain fatty acids or a mixture of synthetic fatty acid esters of medium or long chain fatty acids. In another embodiment, the fatty acid ester is a mixture of fatty acid esters which is not a natural vegetable oil. Natural vegetable oils typically contain 50 to 95% by weight of glycerides of polyunsaturated fatty acids. Exemplary vegetable oils include, but are not limited to, safflower oil, peanut oil, linseed oil, soybean oil, corn oil, and sunflower oil.

Suitable fatty acid esters include, but are not limited to, mono- and diglycerides of capric ($C_{10}$) and caprylic ($C_8$) acids, such as those available under the tradenames CAPMUL® and IMWITOR®. CAPMUL® products are available from Abitec Corporation. IMWITOR® products are available from Sasol.

Exemplary esters include, but are not limited to, CAPMUL® MCM (glyceryl mono and dicaprate), CAPMUL® MCM C8 (glyceryl monocaprylate), CAPMUL® MCM C10 (glyceryl mono and dicaprate); IMWITOR® 988 (caprylic/capric glycerides), IMWITOR® 742 (caprylic/capric glycerides); mono-, di-, and triglycerides of coconut oil (IMWITOR® 928); glyceryl monooleate; glyceryl monolinoleate; propylene glycol esters (CAPMUL® PG-8 (propylene glycol monocaprylate), CAPRYOL™ 90 (propylene glycol monocaprylate 90%), CAPRYOL™ PGMC (propylene glycol caprylate), LABRAFAC™ PG (propylene glycol dicaprylocaprate), LAUROGLYCOL™ 90 (propylene glycol monolaurate), LAUROGLYCOL™ FCC (propylene glycol laurate)); polyethoxylated fatty acid esters (MYRJ 45 (polyethylene glyeol400 monostearate, polyoxy 8 stearate), SOLUTOL® HS 15 (polyethylene glycol 660 hydroxystearate, macrogol 15 hydroxystearate)), and combinations thereof.

When present, the concentration of the one or more esters is from about 1% to about 40% by weight of the fill material, preferably from about 5% to about 35% by weight of the fill material, preferably from about 10% to about 35% by weight of the fill material, more preferably from about 15% to about 35% by weight of the fill material, most preferably from about 20% to about 35% by weight of the fill material. Alternatively, the amount of ester(s) can be expressed as weight percent of the carrier composition (i.e., the fill material absent the active pharmaceutical ingredient). The concentration of the one or more esters in the carrier composition is from about 1% to about 40% by weight of the carrier composition, more preferably from 5% to 35% by weight of the carrier composition, and most preferably from about 10% to about 30% by weight of the carrier composition.

Solutions of progesterone in a fatty acid, such as oleic acid, in the presence of, for example, ethanol and lactic acid, have been found to be physically stable (i.e., no physical change and no precipitation) at a variety of temperatures, for examples from −20° C. to 65° C., even after repeated freeze/thaw cycles.

(d) Other Carrier Components

The carrier composition optionally contains one or more pharmaceutically acceptable additional co-solvents. Exemplary co-solvents include, but are not limited to, polyethoxylated glycerides, Brij™ 97 (polyoxyl 10 oleyl ether, oleth 10, polyethylene glycol monooleyl ether), Cremophor® A 25 (macrogol 25, cetostearyl ether, cetomacrogol), Cremophor® EL (polyoxyl 35 castor oil, glycerol polyethylene, glycol ricinoleate), Cremophor® RH 40 (polyoxyl 40 hydrogenated castor oil, glycerol polyethylene, glycol oxystearate), Labrafil® M 1944 (polyethylene glycol 300 oleic glycerides, oleoyl macrogol-6 glycerides), Labrafil® M 2125 (polyethylene glycol 300 linoleic glycerides, linoleoyl macrogol-6-glycerides), Labrasol® (polyethylene glycol 8 caprylic/capric glycerides, caprylcaproyl polyoxyglycerides), Gelucire® 44/14 (hydrogenated palm kernel oil, polyethylene glycol-32 esters, lauryl polyoxyglycerides, lauryl macrogol glycerides), Gelucire® 50/13 (stearoyl polyoxyglycerides, stearyl macrogolglycerides, D-a-tocopheryl polyethylene glycol 1000 succinate (MW=1513), and combinations thereof.

Antioxidants such as BHA and/or BHT may also be included in the carrier composition to prevent or minimize degradation of the formulation. The concentration of the antioxidant is typically from about 0.001% to about 2%, more preferably from about 0.00 to about 1%, most preferably from about 0.01 to about 0.5% by weight of the carrier.

Other optional ingredients which may be present in the compositions include, but are not limited to, pH stabilizers, thickeners/suspending agents, flavoring agents, sweeteners, and colorants.

3. Other Active Agents

In addition to the sex hormone, the composition may further contain additional therapeutic, prophylactic, diagnostic, and/or nutraceutical agents. Suitable classes of active agents include, but are not limited to, analgesics, anti-inflammatory agents, antihelmintics, anti-arrhythmic agents, antibacterials, anticoagulants, antidepressants, antidiabetics, antiepileptics, antimalarials, antimigraine agents, antihistamines, antihypertensives, antimuscarinic agents, antimycobacterial agents, antineoplastic agents, immunosuppressants agents, antiprotozoal agents, antithyroid agents, antiviral agents, anxiolytic sedatives, astringents, beta adrenoceptor blocking agent, blood products and substitutes, cardiac tonotropic agents, corticosteroids, cough suppressants, diagnostic agents, diuretics, dopaminergics, haemostatics, lipid regulating agents, muscle relaxants, parasympathomimetics, prostaglandins, stimulants and anoretics, sympathomimetics, thyroid agents, and vasodilators.

B. Capsules

The capsule shells are prepared using one or more film forming polymers. Suitable film forming polymers include natural polymers, such as gelatin, and synthetic film forming polymers, such as modified celluloses. Suitable modified celluloses include, but are not limited to, hydroxypropyl methyl cellulose, methyl cellulose, hydroxypropyl methyl cellulose acetate succinate, hydroxypropyl methyl cellulose phthalate, and cellulose acetate phthalate. Hard or soft capsules can be used to administer the hormone. Hard shell capsules are typically prepared by forming the two capsule halves, filling one of the halves with the fill solution, and then sealing the capsule halves together to form the finished capsule. Soft gelatin capsules are typically prepared using a rotary die encapsulation process as described below.

1. Gelatin Capsules

Gelatin is the product of the partial hydrolysis of collagen. Gelatin is classified as either Type A or Type B gelatin. Type A gelatin is derived from the acid hydrolysis of collagen while Type B gelatin is derived from the alkaline hydrolysis of collagen. Traditionally, bovine bones and skins have been used as raw materials for manufacturing Type A and Type B gelatin while porcine skins have been used extensively for manufacturing Type A gelatin. In general, acid-processed gelatins form stronger gels than lime-processed gelatins of the same average molecular weight. The capsules can be formulated as hard or soft gelatin capsules.

2. Non-Gelatin Capsules

Capsules can be prepared from non-gelatin materials, such as carrageenan or modified celluloses. Carrageenan is a natural polysaccharide hydrocolloid, which is derived from seaweed. It includes a linear carbohydrate polymer of repeating sugar units, without a significant degree of substitution or branching. Most, if not all, of the galactose units on a carrageenan molecule possess a sulfate ester group. There are three main types of carrageenan: kappa, iota and lambda; although minor forms called mu and nu carrageenan also exist.

3. Shell Additives

Suitable shell additives include plasticizers, opacifiers, colorants, humectants, preservatives, flavorings, and buffering salts and acids, and combinations thereof.

Plasticizers are chemical agents added to gelatin to make the material softer and more flexible. Suitable plasticizers include, but are not limited to, glycerin, sorbitol solutions which are mixtures of sorbitol and sorbitan, and other polyhydric alcohols such as propylene glycol and maltitol or combinations thereof.

Opacifiers are used to opacify the capsule shell when the encapsulated active agents are light sensitive. Suitable opacifiers include titanium dioxide, zinc oxide, calcium carbonate and combinations thereof.

Colorants can be used to for marketing and product identification/differentiation purposes. Suitable colorants include synthetic and natural dyes and combinations thereof.

Humectants can be used to suppress the water activity of the softgel. Suitable humectants include glycerin and sorbitol, which are often components of the plasticizer composition. Due to the low water activity of dried, properly stored softgels, the greatest risk from microorganisms comes from molds and yeasts. For this reason, preservatives can be incorporated into the capsule shell. Suitable preservatives include alkyl esters of p-hydroxy benzoic acid such as methyl, ethyl, propyl, butyl and heptyl esters (collectively known as "parabens") or combinations thereof.

Flavorings can be used to mask unpleasant odors and tastes of fill formulations. Suitable flavorings include synthetic and natural flavorings. The use of flavorings can be problematic due to the presence of aldehydes which can cross-link gelatin. As a result, buffering salts and acids can be used in conjunction with flavorings that contain aldehydes in order to inhibit cross-linking of the gelatin.

C. Enteric Capsules

Alternatively, the liquid fills can be incorporated into an enteric capsule, wherein the enteric polymer is a component of the capsule shell, as described in WO 2004/030658 to Banner Pharmacaps, Inc. The enteric capsule shell is prepared from a mass comprising a film-forming polymer, an acid-insoluble polymer which is present in an amount making the capsule resistant to the acid within the stomach, an aqueous solvent, and optionally, one or more plasticizers and/or colorants. Other suitable shell additives including opacifiers, colorants, humectants, preservatives, flavorings, and buffering salts and acids may be added.

1. Film-Forming Polymers

Exemplary film-forming polymers can be of natural or synthetic origin. Natural film-forming polymers include gelatin and gelatin-like polymers. Other suitable natural film-forming polymers include shellac, alginates, pectin, and zeins. Synthetic film-forming polymers include hydroxypropyl methyl cellulose, methyl cellulose, hydroxypropyl methyl cellulose acetate succinate, hydroxypropyl methyl cellulose phthalate, cellulose acetate phthalate, and acrylates such as poly (meth)acrylate. The weight ratio of acid-insoluble polymer to film-forming polymer is from about 15% to about 50%. In one embodiment, the film forming polymer is gelatin.

2. Acid-Insoluble Polymers

Exemplary acid-insoluble polymers include cellulose acetate phthalate, cellulose acetate butyrate, hydroxypropyl methyl cellulose phthalate, algenic acid salts such as sodium or potassium alginate, shellac, pectin, acrylic acid-methylacrylic acid copolymers (available under the tradename EUDRAGIT® from Rohm America Inc., Piscataway, N.J. as a powder or a 30% aqueous dispersion; or under the tradename EASTACRYL®, from Eastman Chemical Co., Kingsport, Tenn., as a 30% dispersion). In one embodiment, the acid-insoluble polymer is EUDRAGIT® L100, which is a methacrylic acid/methacrylic acid methyl ester copolymer. The acid-insoluble polymer is present in an amount from about 8% to about 20% by weight of the wet gelatin mass. The weight ratio of acid-insoluble polymer to film-forming polymer is from about 15% to about 50%.

3. Aqueous Solvent

Hard and soft capsules are typically prepared from solutions or suspensions of the film forming polymer and the acid-insoluble polymer. Suitable solvents include water, aqueous solvents, and organic solvents. In one embodiment, the solvent is water or an aqueous solvent. Exemplary aqueous solvents include water or aqueous solutions of alkalis such as ammonia, sodium hydroxide, potassium hydroxide, ethylene diamine, hydroxylamine, tri-ethanol amine, or hydroalcoholic solutions of the same. The alkali can be adjusted such that the final pH of the gelatin mass is less than or equal to 9.0, preferably less than or equal to 8.5, more preferably less than or equal to 8.0. In one embodiment, the alkali is a volatile alkali such as ammonia or ethylene diamine. Upon drying of the finished capsule, the water content of the capsule is from about 2% to about 10% by weight of the capsule, preferably from about 4% to about 8% by weight of the capsule.

4. Plasticizers

Exemplary plasticizers include glycerol, glycerin, sorbitol, polyethylene glycol, citric acid, citric acid esters such as triethylcitrate, polyalcohols with 3-6 carbons and combinations thereof. The plasticizer to polymer (film forming polymer plus acid-insoluble polymer) ratio is from about 10% to about 50% of the polymer weight.

III. Methods of Manufacture

A. Capsule Fill

The fill material is prepared by dissolving the sex hormone, such as progesterone, in the carrier containing a fatty acid solvent, such as oleic acid. The mixture of hormone and fatty acid may be heated to facilitate dissolution of the hormone. Upon cooling to room temperature and encapsulation, the solution remains a liquid. The fill is typically deaerated prior to encapsulation in a soft gelatin capsule. Additional excipients including, but not limited to, co-solvents, antioxidants may be added to the mixture of the hormone and fatty acid. Again the mixture may be heated to facilitate dissolution of the excipients. The progesterone is fully dissolved in the carrier of the present invention and remains so upon storage.

B. Capsule Shell

Gelatin or Non-Gelatin Capsules

The main ingredients of the capsule shell are gelatin (or a gelatin substitute for non-gelatin capsules), plasticizer, and purified water. The primary difference between soft and hard capsules is the amount of plasticizer present in the capsule shell.

Typical gel formulations contain (w/w) 40-50% gelatin, 20-30% plasticizer, and 30-40% purified water. Most of the water is subsequently lost during capsule drying. The ingredients are combined to form a molten gelatin mass using either a cold melt or a hot melt process. The prepared gel masses are transferred to preheated, temperature-controlled, jacketed holding tanks where the gel mass is aged at 50-60° C. until used for encapsulation.

ii. Cold Melt Process

The cold melt process involves mixing gelatin with plasticizer and chilled water and then transferring the mixture to a jacket-heated tank. Typically, gelatin is added to the plasticizer at ambient temperature (18-22° C.). The mixture is cooked (57-95° C.) under vacuum for 15-30 minutes to a homogeneous, deaerated gel mass. Additional shell additives can be added to the gel mass at any point during the gel manufacturing process or they may be incorporated into the finished gel mass using a high torque mixer.

ii. Hot Melt Process

The hot melt process involves adding, under mild agitation, the gelatin to a preheated (60-80° C.) mixture of plasticizer and water and stirring the blend until complete melting is achieved. While the hot melt process is faster than the cold melt process, it is less accurately controlled and more susceptible to foaming and dusting.

iii. Soft Capsules

Soft capsules are typically produced using a rotary die encapsulation process. The gel mass is fed either by gravity or through positive displacement pumping to two heated (48-65° C.) metering devices. The metering devices control the flow of gel into cooled (10-18° C.), rotating casting drums. Ribbons are formed as the cast gel masses set on contact with the surface of the drums.

The ribbons are fed through a series of guide rolls and between injection wedges and the capsule-forming dies. A food-grade lubricant oil is applied onto the ribbons to reduce their tackiness and facilitate their transfer. Suitable lubricants include mineral oil, medium chain triglycerides, and soybean oil. Fill formulations are fed into the encapsulation machine by gravity. In the preferred embodiment, the soft capsules contain printing on the surface, optionally identifying the encapsulated agent and/or dosage.

Upon drying of the finished capsule, the water content of the capsule is from about 2% to about 10% by weight of the capsule, preferably from about 4% to about 8% by weight of the capsule.

C. Enteric Capsules

A method of making an enteric capsule shell is described in WO 2004/030658 to Banner Pharmacaps, Inc. The enteric mass is typically manufactured by preparing an aqueous solution comprising a film-forming, water soluble polymer and an acid-insoluble polymer and mixing the solution with one or more appropriate plasticizers to form a gelatin mass. Alternatively, the enteric mass can be prepared by using a ready-made aqueous dispersion of the acid-insoluble polymer by adding alkaline materials such as ammonium, sodium, or potassium hydroxides or other alkalis that will cause the acid-insoluble polymer to dissolve. The plasticizer-wetted, film-forming polymer can then be mixed with the solution of the acid-insoluble polymer. The mass can also be prepared by dissolving the acid-insoluble polymer or polymers in the form of salts of the above-mentioned bases or alkalis directly in water and mixing the solution with the plasticizer-wetted, film-forming polymer. The mass is cast into films or ribbons using heat controlled drums or surfaces. The fill material is encapsulated in a soft capsule using a rotary die. The capsules are dried under controlled conditions of temperature and humidity. The final moisture content of the shell composition is from about 2% to about 10% by weight of the capsule shell, preferably from about 4% to about 8% by weight by weight of the capsule shell.

Alternatively, release of the sex hormone from the capsule can be modified by coating the capsule with one or more modified release coatings, such as sustained release coatings, delayed release coatings, and combinations thereof.

IV. Methods of Use

Sex hormones can be used to treat a variety of conditions and disorders.

In one embodiment, the sex hormone is progesterone. Progesterone can be used to support pregnancy in Assisted Reproductive Technology (ART) cycles such as In-vitro Fertilization (IVF). Progesterone can be used to control anovulatory bleeding and is also used to prepare uterine lining in infertility therapy and to support early pregnancy. Patients with recurrent pregnancy loss due to inadequate progesterone production may receive progesterone. Progesterone is also used for the prevention of endometrial hyperplasia in nonhysterectomized postmenopausal women who are receiving conjugated estrogen tablets and for treatment of secondary amenorrhea.

The dose of progesterone to be administered can be readily determined by the prescribing physician. In one embodiment, the dose of progesterone is from about 100 mg to about 300 mg, more preferably 100, 200, or 300 mg.

The compositions described herein provide improved dissolution in aqueous media in vitro compared to formulations of hydrophobic drugs suspended in an oil, such as peanut oil. In one embodiment, the compositions described herein release at least about 10%, 20%, 30%, 40%, 50%, 55%, 60%, 65%, 70%, 75%, 80%, 85%, 90%, or 95% of the drug in vitro after 5 minutes in 5% SDS in water or at least about 10%, 20%, 30%, 40%, 50%, 55%, 60%, 65%, 70%, 75%, 80%, 85%, 90%, or 95% of the drug in vitro after 15 minutes in 0.5% SDS in water. In another embodiment, the compositions described herein release at least about 15%, 20%, 25%, 30%, 35%, 40%, 45%, 50%, 55%, 60%, 65%, or 70% of the drug in vitro in fed state simulated intestinal fluid (FeSSIF) after 24 hours.

The capsules described herein exhibit improved dissolution in aqueous media in vitro compared to formulations containing micronized progesterone suspended in an oil, such as peanut oil, such as commercially available formulations sold under the trademark PROMETRIUM®. For example, progesterone dissolved in fatty acid alone, or in combination with CAPMUL® PG-8 and ethanol, release 90% of the progesterone after 15 minutes and 7 minutes, respectively, in 0.5% SDS and 5% SDS in water, respectively. In deaerated water alone, 5.5% of the progesterone was released after 1440 minutes from a two-piece hard shell capsule containing progesterone dissolved in oleic acid, Capmul® PG-8 and ethanol. In contrast, 3% of the progesterone was released from PROMETRIUM® during the same time period.

The capsules described herein should exhibit greater oral bioavailability and less interpatient and intrapatient invariability in vivo then formulations containing a micronized active agent, such a progesterone, suspended in an oil carrier, such as peanut oil. Further, the absence of oil-based carriers, such as peanut oil, should minimize or prevent allergic reactions.

The invention will now be illustrated by the following non-limiting examples in which all parts are by weight unless otherwise indicated.

EXAMPLES

Example 1

Fill Materials Containing Progesterone Dissolved in Fatty Acid-Based Vehicles

Three formulations were prepared by dissolving progesterone in various oleic acid-based vehicles. The ingredients present in the formulations and their amount by weight in grams and their percent weight of the carrier material (including the API) are shown in Table 2.

TABLE 2

Percentage of each ingredient in different progesterone solutions

| Ingredient | Amount (g) (% in carrier composition) | | |
|---|---|---|---|
| | Formulation 1 | Formulation 2 | Formulation 3 |
| Oleic acid | 745.5 (74.58%) | 600 (75.0%) | 596 (83.9%) |
| Lactic acid | 64 (6.4%) | 100 (12.5%) | 44 (6.2%) |
| Ethanol | 90 (9%) | 100 (12.5%) | 70 (8.8%) |
| Progesterone (API) | 100 | 100 | 70 |
| Total wt. | 999.6 | 900 | 780 |
| w/w of API in fill | 10.0% | 11.1% | 9.0% |

Formulations 1-3 were prepared as follows:

Formulation 1

745.5 g of oleic acid (Penta Manufacturing, NF grade) and 64 g of lactic acid (Penta Manufacturing, 88% natural) were mixed together at room temperature until the mixture was visually uniform. 100 g of progesterone powder (Pfizer Inc, USP grade) was added to the mixture and stirred at 60 rpm at 45° C. until completely wetted. The stirring was continued for at least 30 minutes, until a semi-transparent solution was obtained. The semi-transparent solution was cooled to room temperature. 90 g of ethanol (190 Proof, Pharmco) was added to the mixture and the mixture was stirred for another 10 minutes until a clear solution was obtained.

Formulation 2

600 g of oleic acid and 100 g of lactic acid were mixed together at room temperature until the mixture was visually uniform. 100 g of progesterone powder was added to the mixture and stirred at 60 rpm at 45° C. until completely wetted. The stirring was continued for at least 30 minutes, until a semi-transparent solution was obtained. The semi-transparent solution was cooled to room temperature. 100 g of ethanol was added to the mixture and the mixture was stirred for another 10 minutes until a clear solution was obtained.

Formulation 3

596 g of oleic acid and 44 g of lactic acid were mixed together at room temperature until the mixture was visually uniform. 70 g of progesterone powder is added into the mixture and stirred at 60 rpm at 45° C. until completely wetted. The stirring was continued for at least 30 minutes, until a semi-transparent solution was obtained. The semi-transparent solution was cooled to room temperature. 70 g of ethanol was added to the mixture and the mixture was stirred for another 10 minutes until a clear solution was obtained.

Phase Stability of the Formulations

40° C. for Three Weeks

The above solutions were divided into portions of about 5 grams each, which are added to 20 ml clear glass scintillation vials with proper capping. The vials were put into a 40° C. oven for three weeks. All the solutions remained clear.

Room Temperature for 10 Weeks

Vials containing approximately 5 grams of Formulations 1-3 were kept at room temperature for 10 weeks. The solutions remained clear for at least 10 weeks.

Refrigeration for 3 Days

Another batch of vials was put under refrigeration (0 to −4° C.) for three days, then equilibrated to room temperature for 3 days. The solution formed an opaque semi-solid under refrigerated conditions, but melted to form a clear solution at room temperature. The cycle of refrigeration and thawing (at room temperature) was repeated five times. At the end of the five cycles, the formulation remained a clear solution.

Refrigeration for 8 Weeks

Another batch of vials was kept under refrigeration (0 to −4° C.) over 8 weeks, then equilibrated to room temperature. The solution formed an opaque semi-solid at refrigerated conditions, but melted to form a clear solution at room temperature.

Example 2

Fill Materials Containing Progesterone Dissolved in a Fatty Acid-Based Vehicle Containing Capmul® PG-8

A formulation containing progesterone dissolved in a fatty acid and further containing CAPMUL® PG-8 was prepared (Formulation 4). The ingredients and their amounts are shown in Table 3.

TABLE 3

Composition of Progesterone Solution-Formulation 4

| Ingredient | Quantity (g) (% in carrier composition) |
|---|---|
| Progesterone | 100 g |
| Oleic acid | 594 g (64.8%) |
| Lactic acid | 20.9 g (2.3%) |
| CAPMUL ® PG-8 | 302.3 g (33.0%) |
| % progesterone (w/w) in fill | 9.8% |

Formulation 4 was prepared as follows. 594 g of oleic acid and 20.9 g of lactic acid were mixed together until the mixture was visually uniform. 100 g of progesterone powder was added to the mixture and stirred at 60 rpm until completely wetted. 302.3 g of CAPMUL® PG-8 (Abitech, NF grade) was added with stirring and the stirring was continued for at least 15 minutes, until a clear solution was obtained.

Example 3

Fill Materials Containing Progesterone Dissolved in a Fatty Acid-Based Vehicle Containing Capmul® PG-8 and Ethanol A formulation containing progesterone dissolved in a fatty acid and further containing Capmul® PG-8 and ethanol was prepared (Formulation 5). The ingredients and their amounts are shown in Table 4.

TABLE 4

Composition of Progesterone Solution-Formulation 5

| Ingredients | Quantity (g) (% in carrier) |
|---|---|
| Progesterone | 100 g |
| Oleic acid | 596 g (64.7%) |
| Lactic acid | 22.6 g (2.4%) |
| Ethanol | 49.7 g (5.4%) |
| CAPMUL ® PG-8 | 253 g (27.5%) |
| % progesterone (w/w) in fill | 9.8% |

Formulation 5 was prepared as follows. 596 g of oleic acid and 22.6 g of lactic acid were mixed together until the mixture was visually uniform. 100 g of progesterone powder was added to the mixture and stirred at 60 rpm until completely wetted. 253 g of CAPMUL® PG-8 was added with stirring and the stirring was continued for at least 15 minutes, until a clear solution was obtained. 49.7 g of ethanol was added to the mixture and stirred for another 10 minutes.

Phase Stability of the Formulations

40° C. for Three Weeks

Formulations 4 and 5 were divided into portions of about 5 grams each, which were added to 20 ml clear glass scintillation vials with proper capping. The vials were put into a 40° C. oven for three weeks. All the solutions remained clear.

Room Temperature for 10 Weeks

Vials containing aliquots of formulations 4 and 5 were kept at room temperature and remained clear for at least 10 weeks.

Refrigeration for 3 Days

Another batch of vials containing formulations 4 and 5 was put under refrigeration (0 to −4° C.) for 3 days and then equilibrated to room temperature for 3 days. The solutions formed an opaque semi-solid under refrigerated conditions, but melted to form a clear solution at room temperature. The cycle of refrigeration and thawing (at room temperature) was repeated five times. At the end of these five cycles, the formulations remained clear solutions.

Refrigeration for 8 Weeks

Another batch of vials was kept under refrigeration (0 to −4° C.) for 8 weeks and then equilibrated to room temperature. The solutions formed an opaque semi-solid under refrigerated conditions, but melted to form a clear solution at room temperature.

Example 4

Progesterone Compatibility with Various Solubilizers

The progesterone formulation prepared in Example 3 was divided into portions of about 5 grams each, which were added to 20 ml glass scintillation vials with caps. The vials were put into an oven set at 65° C. One set was heated for 7 days. The samples were assayed for progesterone content by HPLC, using a procedure adapted from the USP method. The chromatographic conditions were as follows:

Column: Zorbax SB-C8, 250×4.6 mm, 5—micron or equivalent,

Column Temperature: 30° C.,

Flow rate: 1.5 ml/min, Injection Volume: 10 μl, Detector Wavelength: 254 nm.

Mobile Phase Acetonitrile:Water (60:40)

TABLE 5

Assay Recovery of stressed Progesterone formulation

| Sample ID | Storage condition | T = 1 week |
|---|---|---|
| Progesterone Solution, Example 3 | Room Temperature | 100% |
| | 65° C. | 92.4% |

As shown in Table 5, the excipients used in Formulation 5 are compatible with progesterone, without significant loss of potency, even after one week at 65° C., compared to samples stored at room temperature.

Example 5

Encapsulation of Progesterone Solutions in Two Piece Hard Gelatin Capsules and Softgel Capsules The formulations described in. Examples 1-4 were encapsulated in hard gelatin capsules and softgel capsules as follows.

Hard Capsules

The progesterone solution of Example 3 (Formulation 5) was added to empty hard gelatin capsules (Size Number 1, made by Eli Lilly and Company, Indianapolis, Ind.). Three capsules are filled with 1.0 grams of the fill solution, which contained approximately 83 mg progesterone.

Softgel Capsules

The progesterone solution of Example 1 (Formulation 1) and Example 3 (Formulation 5) were each encapsulated in softgel capsules.

Preparation of gelatin: Bovine gelatin, extracted from bones, was mixed with the appropriate amount of glycerin and water. The mixture was heated to 70° C. under continuous mixing for 24 hours, and then cooled to about 60° C. The gelatin mixture was added to the containers of an encapsulation machine. The ribbon thickness was maintained at 0.030 inches. The die size was 22 oblong. The fill weight was 1021 mg and the capsules contained approximately 100 mg of progesterone. The softgel capsules were dried for two weeks to obtain a hardness of 9 Newtons.

Dissolution tests, assays, and stability tests were carried out on the softgel capsules. To assess phase stability e.g., precipitation of the drug substance in the carrier over a prolonged period of time, the capsules were stored at room temperature for up to 8 months and ten days. The capsules were cut open and the fill materials observed visually. No precipitate or insoluble materials were observed in either of the formulations over the time periods observed.

Example 6

Comparative In Vitro Release Studies of Progesterone Solutions Encapsulated in Softgel Capsules Dissolution studies were performed using USP Dissolution Apparatus II (paddle @100 rpm) using various dissolution media containing various levels of sodium dodecyl sulfate (SDS) in de-aerated water as described below. The volume of the dissolution medium used was 900 mL. All dissolution experiments were carried out at 37° C. At predetermined time intervals (5, 15, 30, 45, 60, 120, 180, 240, 300, and 1440 minutes) aliquots were taken and assayed. The samples were assayed for progesterone concentration in the dissolution media by HPLC using an Agilent ChemStation under the conditions described in Example 4. The results are shown in FIGS. 1-3.

The dissolution study in an aqueous medium containing 5% SDS (FIG. 1) shows the complete dissolution of the formulation described in Example 3 (Formulation 5) within 5 minutes, while PROMETRIUM® takes almost 24 hours to reach the same degree of dissolution.

Figure 2:
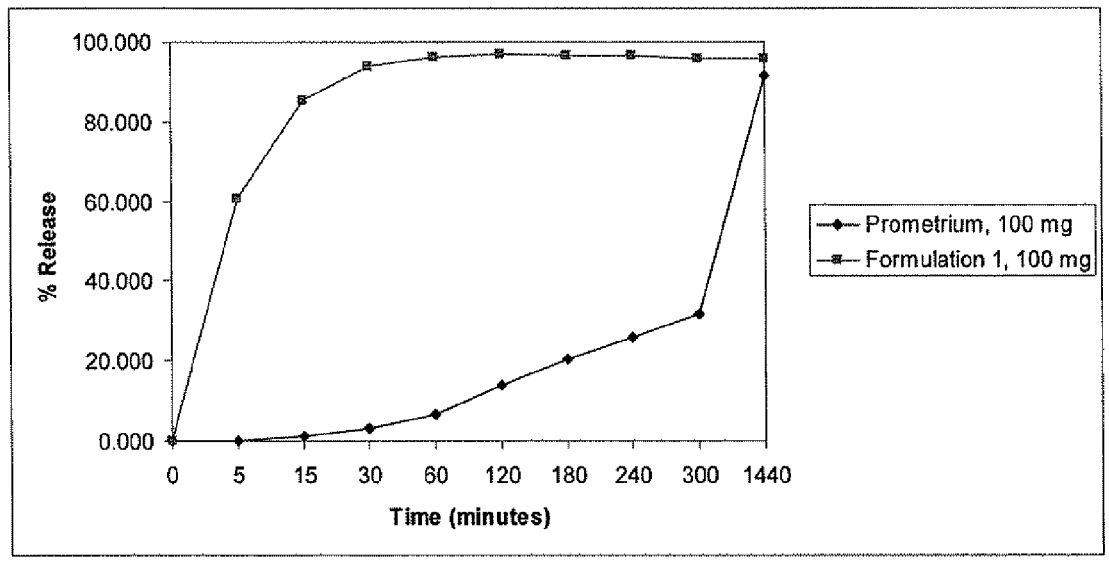
FIG. 2 is a graph comparing the in vitro release profile of progesterone (percent release) dissolved in oleic acid and encapsulated in a softgel capsule to the in vitro release profile of PROMETRIUM® (micronized progesterone suspended in peanut oil and encapsulated in a softgel capsule) in 0.5% sodium dodecyl sulfate (SDS) in water as a function of time (minutes) in a USP Apparatus II at 37±0.5° C. and 100 RPM.
Figure 3:
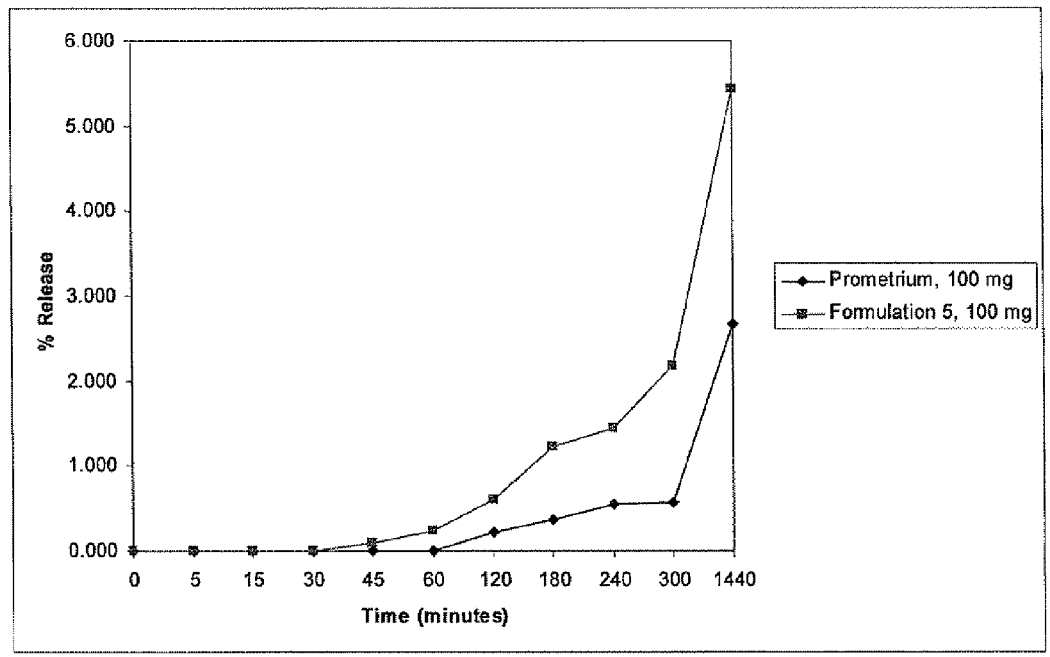
FIG. 3 is a graph comparing the in vitro release profile of progesterone (percent release) dissolved in a mixture of oleic acid, Capmul® PG-8 and ethanol and encapsulated in a soft-gel capsule to the in vitro release profile of PROMETRIUM® (micronized progesterone suspended in peanut oil encapsulated in a softgel capsule) in deaerated water as a function of time (minutes) in a USP Apparatus II at 37±0.5° C. and 100 RPM.

The results of the dissolution study performed in an aqueous medium containing 0.5% SDS are shown in FIG. 2. The formulation of Example 1 (Formulation 1) was compared to commercially available progesterone PROMETRIUM®. This formulation was shown to have much faster onset and fuller dissolution, compared to PROMETRIUM®.

A study was also performed using deareated water only (no surfactant). The formulation of Example 3 (Formulation 5) was compared to commercially available progesterone PROMETRIUM®. The results are shown in FIG. 3. Formulation 5 has a much faster dissolution onset and a higher overall dissolution rate. After 1440 minutes, Formulation 5 released twice as much progesterone than PROMETRIUM™.

Example 7

Comparative In Vitro Release Studies (FeSSIF) of Progesterone Solutions Encapsulated in Softgel Capsules Dissolution studies were performed using progesterone capsules prepared according to Example 3 (Formulation 5, 100 mg/capsule) and PROMETRIUM® capsules in Fed State Simulated Intestinal Fluid (FeSSIF) dissolution media containing the components shown in Table 6.

TABLE 6

FeSSIF Media Components with pH adjusted to 7.5 using either acetic acid or 5M NaOH

| Ingredients | Concentration |
|---|---|
| Taurocholic Acid | 15 mM |
| Lactic Acid | 20 mM |
| NaOH (pellets) | 0.404% (w/w) |
| Acetic Acid | 100 mM |
| NaCl | 1.1874% (w/w) |

Figure 4:
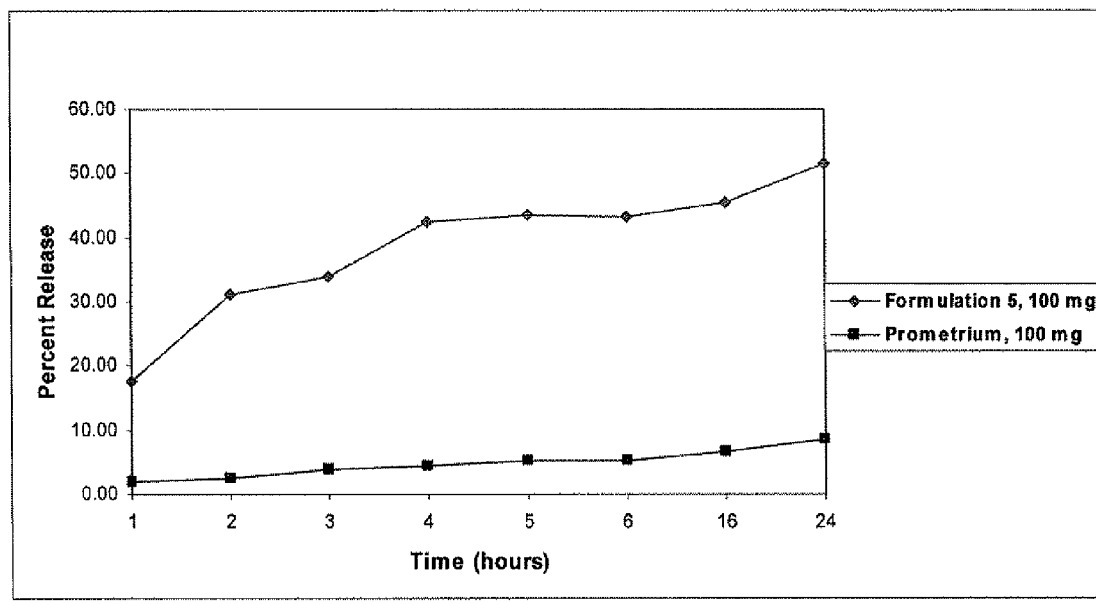
FIG. 4 is a graph comparing the in vitro release profiles (percent released) of progesterone capsules containing oleic acid, lactic acid, ethanol, and Capmul PG-8 and PROMETRIUM® (micronized progesterone suspended in peanut oil encapsulated in a softgel capsule) in Fed State Simulated Intestinal Fluid (FeSSIF) in a USP Apparatus II at 37±0.5° C. and 100 RPM.

The dissolution was performed at 37° C. using USP Apparatus II (paddle) at 50 rpm in 1000 ml of the dissolution medium. The dissolution results are shown in FIG. 4. As shown in this figure, the amount of progesterone released from Formulation 5 in FeSSIF medium was about 4 to 5 times higher than that released from PROMETRIUM® capsules. The cumulative release at the end of 24 hours from Formulation 5 was about 51% versus less than about 10% from PROMETRIUM®.

In conclusion, the results of the dissolution assays of the formulations described in the examples, compared with commercially available progesterone (PROMETRIUM®) demonstrate that the formulations described herein have a higher dissolution rate and faster onset of dissolution. Extrapolation suggests that that the formulations described herein will exhibit increased bioavailability in vivo and attendant faster therapeutic response.

Unless defined otherwise, all technical and scientific terms used herein have the same meanings as commonly understood by one of skill in the art to which the disclosed invention belongs. Publications cited herein and the materials for which they are cited are specifically incorporated by reference. Those skilled in the art will recognize, or be able to ascertain using no more than routine experimentation, many equivalents to the specific embodiments of the invention described herein. Such equivalents are intended to be encompassed by the following claims.

We claim:

1. A hard or soft capsule comprising a shell and a liquid fill material, the liquid fill material comprising from about 7% to about 50% by weight of the fill of progesterone, wherein the progesterone is dissolved in a carrier comprising
   from about 60% to about 95% by weight of one or more pharmaceutically acceptable fatty acids;
   the fill comprising excipients enhancing dissolution of the progesterone consisting of
   (a) from about 1% to about 20% by weight of one or more pharmaceutically acceptable organic acids selected from C1 to C 12 acids;
   (b) from about 1% to about 20% by weight of one or more pharmaceutically acceptable alcohols selected from C1 to C6 alcohols; and
   (c) from about 1% to about 40% by weight of one or more pharmaceutically acceptable mono, di- or tri-ester of medium or long chain fatty acids.

2. The capsule of claim 1, wherein the concentration of progesterone is from about 7% to about 15% by weight of the fill material.

3. The capsule of claim 1, wherein the concentration of progesterone is from about 8% to about 12% by weight of the fill material.

4. The capsule of claim 1, wherein the concentration of progesterone is from about 9% to about 11% by weight of the fill material.

5. The capsule of claim 1, wherein the one or more fatty acids are selected from the group consisting of oleic acid, linoleic acid, myristoleic acid, palmitoleic acid, arachidonic acid and combinations thereof.

6. The capsule of claim 5, wherein the concentration of the one or more fatty acids is from about 65% to about 80% by weight of the carrier.

7. The capsule of claim 6, wherein the concentration of the one or more fatty acids is from about 65% to about 75% by weight of the carrier.

8. The capsule of claim 1, wherein the one or more organic acids is selected from the group consisting of lactic acid, acetic acid, glycolic acid, propionic acid, isobutyric acid, butyric acid, isovaleric acid, valeric acid, caproic acid, succinic acid, and combinations thereof.

9. The capsule of claim 8, wherein the concentration of the one or more alcohols is from about 2% to about 18% by weight of the carrier.

10. The capsule of claim 9, wherein the concentration of the one or more organic acids is from about 3% to about 15%.

11. The capsule of claim 1, wherein the one or more alcohols is selected from the group consisting of ethanol, isopropanol, isobutanol, butanol, t-butanol, glycerol, propylene glycol, and combinations thereof.

12. The capsule of claim 11, whereint he concentration of the one or more alcohols is from about 2% to about 18% by weight of the carrier.

13. The capsule of claim 12, wherein the concentration of the one or more alcohols is from about 5% to about 15%.

14. The capsule of claim 1, wherein the one or more mono, di or tri ester of medium or long chain fatty acids is selected from the group consisting of mono and diglycerides of capric and caprylic acids, mono, di and tri glycerides of coconut oil, glyceryl monooleate, glyceryl monolinoleate, propylene glycol monocaprylate, propylene glycol caprylate, propylene glycol dicaprylocaprate, propylene glycol monolaurate, propylene glycol laurate, polyethoxylated fatty acid esters, polyethylene glycol monostearate, polyoxy stearate, polyethylene glycol hydroxystearate, macrogol hydroxystearate, and combinations thereof.

15. The capsule of claim 14, wherein the concentration of the one or more mono, di or tri ester of medium or long chain fatty acids is from about 5% to about 35% by weight of the carrier.

16. The capsule of claim 15, wherein the concentration of the one or more mono, di or tri ester of medium or long chain fatty acids is from about 10% to about 30% by weight of the carrier.

17. The capsule of claim 1, wherein the concentration of progesterone is from about 9% to about 11% by weight of the fill material, the fatty acid is oleic acid present from about 65% to about 75% by weight of the carrier, the organic acid is lactic acid present at about 3% to about 15% by weight of the carrier, and the alcohol is ethanol present at about 5% to about 15% by weight of the carrier.

18. The capsule of claim 1, wherein the concentration of progesterone is from about 9% to about 11% by weight of the fill material, the fatty acid is oleic acid present from about 65% to about 75% by weight of the carrier, the organic acid is lactic acid present at about 3% to about 15% by weight of the carrier, and the mono, di or tri ester of a fatty acid is propylene glycol monocaprylate present at about 10 to about 30% by weight of the carrier.

19. The capsule of claim 1, wherein the capsule shell is a hard capsule shell.

20. The capsule of claim 1, wherein the capsule shell is a soft capsule shell.

21. The capsule of claim 20, wherein the capsule shell is a gelatin shell.

22. The capsule of claim 20, wherein the capsule shell is a non-gelatin shell.

23. The capsule of 1, wherein the capsule is an enteric capsule.

24. The capsule of claim 1, wherein the capsule is coated with an enteric coating.

25. The capsule of claim 23, wherein an enteric polymer is a component of the capsule shell.

26. A method of making a hard or soft capsule of claim 1, comprising fully dissolving the progesterone to about 7% to about 50% of the fill comprising one or more fatty acids in an amount of the fill from about 60% to about 95% by weight and adding excipients enhancing dissolution of the progresterone consisting of
   from about 1% to about 20% by weight of one or more pharmaceutically acceptable organic acids selected from C1 to C12 acids;
   from about 1% to about 20% by weight of one or more pharmaceutically acceptable alcohols selected from C1 to C6 alcohols; and
   from about 1% to about 40% by weight of one or more pharmaceutically acceptable mono, di- or tri-ester of medium or long chain fatty acids, optionally, one or more co-solvents,
   adding and encapsulating the fill material in a hard or soft capsule.

27. A method of administering progesterone to a patient in need thereof, the method comprising administering the hard or soft capsule of claim 1.

28. The method of claim 27, wherein the capsule exhibits increased bioavailability in vivo compared to a softgel capsule encapsulating micronized progesterone suspended in peanut oil.

29. The method of claim 27, wherein the capsule exhibits less interpatient and intrapatient variability compared to a softgel capsule encapsulating micronized progesterone suspended in peanut oil.

* * * * *

UNITED STATES PATENT AND TRADEMARK OFFICE
CERTIFICATE OF CORRECTION

PATENT NO. : 9,011,908 B2  
APPLICATION NO. : 12/752629  
DATED : April 21, 2015  
INVENTOR(S) : Zhi Liu et al.

Page 1 of 1

It is certified that error appears in the above-identified patent and that said Letters Patent is hereby corrected as shown below:

IN THE SPECIFICATION  
Column 1, line 51, replace "Table1" with --Table 1--.  
Column 4, line 2, replace "by weigh" with --by weight--.  
Column 5, line 30, delete "PROMETRIUMTNI".  
Column 6, line 23, replace "a molecules" with --a molecule--.  
Column 7, line 11, replace "by weigh" with --by weight--.  
Column 8, line 61, replace "examples" with --example--.  
Column 13, line 3, replace "by weight by weight" with --by weight--.  
Column 13, line 60, replace "then" with --than--.  
Column 17, line 19, replace "described in. Examples" with --described in Examples--.  
Column 18, line 22, replace "as much progesterone than" with --as much progesterone as--.  
Column 18, line 62, replace "suggests that that the" with --suggests that the--.

IN THE CLAIMS  
Claim 9, column 19, line 51, replace "alcohols" with --organic acids--.  
Claim 26, column 20, line 51, replace "progesterone" with --progesterone--.

Signed and Sealed this  
Sixth Day of October, 2015

Michelle K. Lee  
*Director of the United States Patent and Trademark Office*